United States Patent
Grimes et al.

(10) Patent No.: US 6,429,349 B1
(45) Date of Patent: *Aug. 6, 2002

(54) CO-ALKYLATION FOR GASOLINE RVP REDUCTION

(75) Inventors: Lewis E. Grimes, Glen Ellyn; R. L. Mehlberg, Wheaton; V. J. Kwasniewski, Northbrook; James B. Young, Cresthill; John V. Bartels, Chicago, all of IL (US)

(73) Assignee: BP Corporation North America Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/695,868

(22) Filed: Aug. 12, 1996

(51) Int. Cl.[7] .............................. C07C 2/56; C07C 2/58

(52) U.S. Cl. ...................... 585/719; 585/709; 585/721; 585/723; 585/730

(58) Field of Search ................. 585/709, 721, 585/723, 730, 719, 731

(56) References Cited

U.S. PATENT DOCUMENTS

| | | | | |
|---|---|---|---|---|
| 3,657,109 A | * | 4/1972 | Beyaert ...................... 208/80 |
| 4,429,173 A | * | 1/1984 | Hutson, Jr. et al. ......... 585/723 |
| 5,382,744 A | * | 1/1995 | Abbott et al. ............... 585/709 |
| 5,583,275 A | * | 12/1996 | Kranz et al. ................ 585/709 |

* cited by examiner

*Primary Examiner*—Thuan D. Dang
(74) *Attorney, Agent, or Firm*—Patrick J. Kim

(57) ABSTRACT

Methods and apparatus that are used in an alkylation reactor system for adding low purity isopentane to alkylation reactor feed to block formation of isopentane, resulting in high incremental isopentane conversion and minimal octane and C5+ yield loss, and low acid consumption from C6+ isoparaffins with superior yields.

10 Claims, 6 Drawing Sheets

US 6,429,349 B1

CO-ALKYLATION FOR GASOLINE RVP REDUCTION

FIELD OF THE INVENTION

The present invention relates to the effective alkylation of isopentane to reduce the Reid vapor pressure (RVP) of the resulting alkylate, and more particularly to the alkylation of isopentane in combination with isobutane to reduce alkylate RVP.

BACKGROUND OF THE INVENTION

Isopentane, a product of many refinery processes, including alkylation, is a major contributor to refinery gasoline pool RVP because of its high RVP of 20.5 pounds per square inch (PSI). Alkylation of isopentane is one way to reduce its RVP. However, alkylation of pure isopentane or suppression of isopentane from amylene alkylation results in low $C_5+$ yields, low octanes and low isopentane conversion.

Classic studies of alkylation show that isopentane reacts readily to form alkylates that are generally one carbon number larger than isobutane alkylates and slightly lower in octane. Historically, however, isopentane has not been alkylated because of its high value as a gasoline blendstock, relative to isobutane, and the lower value of isopentane alkylates relative to isobutane alkylates.

In fact, isopentane alkylation has been so unfavorable economically in the non-reformulated gasoline technologies that studies of the concurrent alkylation of isobutane and isopentane have not been published, only studies in which single isoparaffins were fed. This is important because past work has overlooked possible synergies resulting from interaction between isobutane and isopentane alkylation.

SUMMARY OF THE INVENTION

It has been discovered that the addition of small amounts of impure isopentane, with isopentane:olefin ratios on the order of 0.1 to 2.0, to conventional isobutane alkylation, with isobutane:olefin ratios on the order of above 5, of mixed butylene and amylene olefins gives superior $C_5+$ yields, octanes, and isopentane conversion to other methods of isopentane conversion, on the order of 16 to 40 percent.

In a general sense, the invention comprises a method of alkylating a mixture comprising olefins having from about 3 to 5 carbon atoms per molecule ($C_3$ to $C_5$ olefins) by mixtures of isobutane and isopentane with an acid catalyst to form a high octane alkylate that has relatively low Reid vapor pressure, comprising the steps of: charging a mixed $C_3$ to $C_5$ olefin stream with an isobutane stream to form an isobutane-charged alkylation feed; charging said isobutane-charged alkylation feed with an isopentane stream to form a mixed isoparaffin-charged alkylation feed; and reacting said mixed isoparaffin-charged alkylation feed with an acid catalyst to form an alkylate that has high octane combined with low Reid vapor pressure. The invention also comprises apparatus for implementing this process.

DETAILED DESCRIPTION OF THE PREFERRED EMBODIMENT

Figure 1:
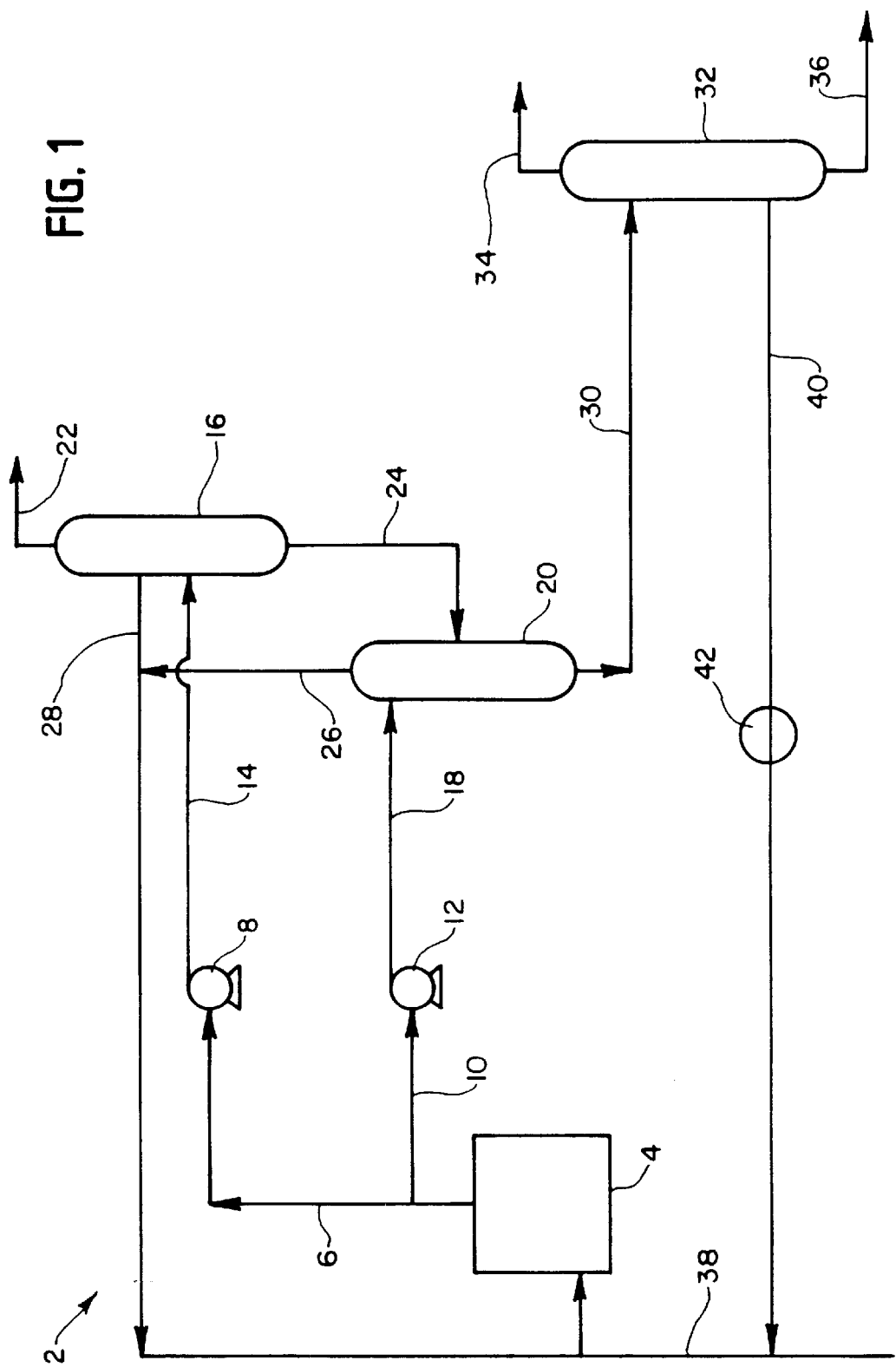
FIG. 1 is a schematic representation of an alkylation reactor system modified to incorporate the invention.

Referring to the drawings, wherein reference characters indicate like or corresponding parts throughout the views, FIG. 1 shows a schematic representation of an alkylation reactor system 2 according to the invention. A standard reactor unit 4 produces settler effluent that is directed through an output stream 6 comprising settler effluent that feeds a first pump 8 and an output stream 10 that feeds a second pump 12. An output stream 14 from the first pump 8 feeds a standard alkylate depropanizer unit 16. An output stream 18 from the second pump 12 feeds a standard alkylate deisobutanizer unit or isobutane stripper 20.

Propane is taken off the top of the depropanizer 16 in an output stream 22. Bottoms product is taken from the depropanizer 16 in an output stream 24 that is fed into the deisobutanizer 20. Isobutane is taken off the top of the deisobutanizer 20 in an output stream 26 and recycled back to the reactor 4. Optionally, isobutane is also taken as a sidedraw from the depropanizer 16 and recycled back to the reactor 4 through an output stream 28.

Bottoms product is taken from the deisobutanizer 20 in an output stream 30 and fed to a standard alkylate debutanizer 32. Butane is taken off the top of the debutanizer 32 in an output stream 34. Debutanized alkylate is taken from the bottom of the debutanizer 32 in an output stream 36.

In FIG. 1, low purity isopentane is supplied to the alkylation reactor system from a variety of sources. Streams that are relatively rich in isobutane and isopentane, such as those produced by modified operations of debutanizers on isomerate or reformate, can be charged directly to the reactor unit 4 through an input stream 38. Table 1 shows an isopentane-rich stream produced by modified operations of an isomerate debutanizer.

In addition, isopentane-rich amylenes from fluid catalytic cracking operations or TAME (Tertiary-Amyl-Methyl-Ether) manufacture may also be charged directly to the reactor unit 4 through the input stream 38. Other sources of dilute isopentane suitable for charging the reactor unit 4 are light virgin naphtha (LVN), debutanized natural gasoline (DBG), light catalytic naphtha, and light coker naphtha.

Dilute isopentane, wherein isopentane concentration is approximately three percent or less, can also be enriched to 40 percent or more and recovered from the alky reactor effluent, or from low isopentane content streams by the addition of a vapor sidedraw to the alkylate debutanizer. In FIG. 1, enriched isopentane from a vapor sidedraw on the debutanizer 32 is charged directly to the reactor unit 4 through an outlet stream 40 that connects to the inlet stream 38. Heat from the enriched isopentane sidedraw is conveniently transferred from the outlet stream 40 to heat the deisobutanizer 20 with a standard heat exchanger 42.

It has been observed that most alkylation occurs at the inlet of the reactor unit 4, just as the olefin contacts the catalyst. In order to maximize the localized isopentane:olefin ratio at this point, it is desirable to inject the dilute isopentane stream into the alky feed as it enters the reactor. Thus, a staged olefin feed, with the isobutane stream injected first, before the alky feed reaches the reactor, followed by injection of the isopentane-olefin stream into the alky feed as it enters the reactor, is preferred.

Any of the well known alkylation catalysts are suitable for this invention. In particular, hydrofluoric acid, sulfuric acid, and the various halogenated sulfuric and halogenated sulfonic acids generally that are commonly used in the alkylation process.

Figure 2:
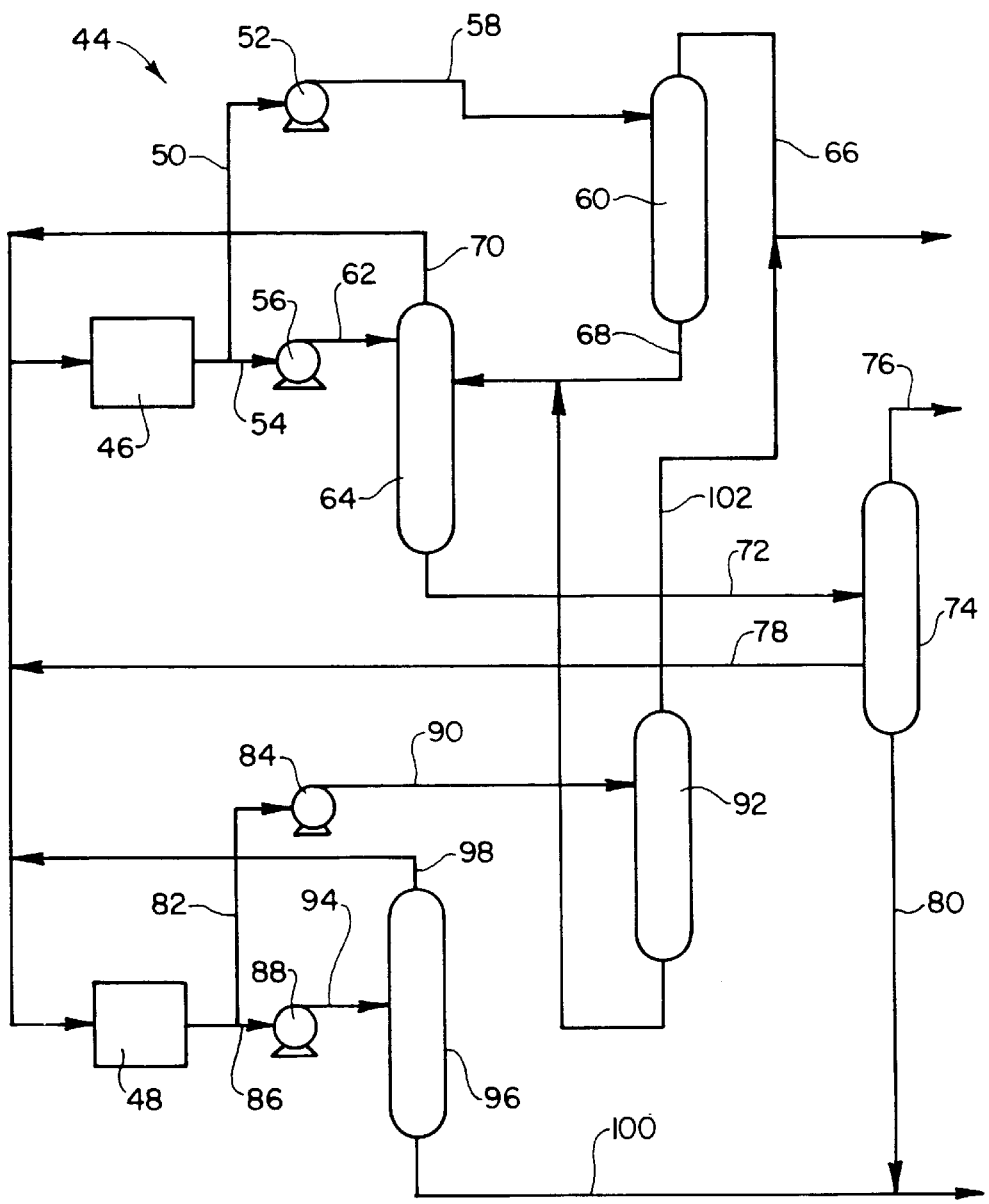
FIG. 2 is a schematic representation of a dual alkylation reactor system modified to incorporate the invention.

In refineries with two deisobutanizer towers, isopentane can also be recycled in high yield and high purity by converting one of the alkylate deisobutanizers to a deisopentanizer. FIG. 2 shows an alkylate reactor system 44 that comprises two reactor units 46 and 48. The reactor units 46 and 48 need not be identical. Likewise, the catalysts used therefor need not be identical.

The reactor unit 46 provides settler effluent through an output stream 50 that feeds a first pump unit 52 and effluent through an output stream 54 that feeds a second pump unit 56. An output stream 58 from the first pump 52 feeds a first standard depropanizer unit 60. An output stream 62 from the second pump 56 feeds a standard deisobutanizer unit 64.

Propane is taken off the top of the first depropanizer 60 in an output stream 66. Bottoms product is taken from the first depropanizer 60 in an output stream 68 that is fed into the deisobutanizer 64. Isobutane is taken off the top of the deisobutanizer 64 in an output stream 70 and recycled back to the reactor units 46 and 48. In case one of the reactor units 46 and 48 is refrigerated, its associated depropanizer woud be fed a portion of the refrigerant and depropanizer bottoms product would be returned to the reactors 46 and 48.

Bottoms product from the deisobutanizer 64 is fed in an output stream 72 to a standard debutanizer 74. Butane is drawn from the top of the debutanizer 74 in an output stream 76. Dilute isopentane is taken from a vapor sidedraw on the deisobutanizer 74 and charged directly to the reactor units 46 and 48 through an output stream 78. Debutanized alkylate is taken from the bottom of the debutanizer 74 in an output steam 80.

The reactor unit 48 provides settler effluent through an output stream 82 that feeds a third pump unit 84 and through an output stream 86 that feeds a fourth pump unit 88. An output stream 90 from the third pump 84 feeds a second standard depropanizer unit 92. An output stream 94 from the fourth pump 88 feeds a standard deisobutanizer unit that is modified to operate as a deisopentanizer 96.

Isopentane is taken off the top of the deisopentanizer 96 in an output stream 98 and fed back to the reactor units 46 and 48. Deisopentanized alkylate is taken from the bottom of the deisopentanizer 96 in an output stream 100 to combine with the debutanized alkylate in the output stream 80 from the debutanizer 74. Propane is taken off the top of the second depropanizer 92 in an output stream 102 that combines with the propane in the output stream 66 from the first depropanizer 60.

General

The terms "$nC_x$", where x is number from 3 to about 11, are used herein to identify normal hydrocarbon compounds having from 3 to about 11 carbon atoms per molecule. Terms "$nC_x+$", where x is number from 3 to about 11, are used herein to identify normal hydrocarbon compounds having x and greater number of carbon atoms per molecule Terms "$iC_x$", where x is number from 3 to about 11, are used herein to identify isomers of hydrocarbon compounds having from 3 to about 11 carbon atoms per molecule. The term "2.3 DMB" is 2,3-Dimethylbutane. The term "2.2 DMB" is 2,2-Dimethylbutane. The term "cC5" is Cyclopentane. The term "MCP" is Methylcyclopentane. The term "2 MP" is 2-Methylpentane, and the term "3 MP" is 3-Methylpentane. BPH is barrels (of 42 gallon each) per hour, and B/D is barrels per day.

EXAMPLE 1

In applying the invention to an existing sulfuric alkylation reactor system, dilute isopentane recovered from the vapor sidedraw of the debutanizer and charged back to the input stream of the reactor as described above in connection with FIG. 1 was concentrated over fifteen times and recycled to extinction. Refrigeration horsepower increase is negligible.

Conditions before and after isopentane recycle are summarized as follows:

|  | BEFORE RECYCLE | AFTER RECYCLE | |
| --- | --- | --- | --- |
|  |  | Extinction $iC_5$ Recycle | 50 Percent $iC_5$ Recycle |
| Reactor Effluent: |  |  |  |
| Composition (Vol %) |  |  |  |
| $nC_4$ | 9.6 | 9.4 | 9.4 |
| $iC_4$ | 56.8* | 56.8* | 56.8 |
| $nC_5$ | 11.9 | 12.0 | 12.0 |
| $iC_5$ | 1.5 | 4.4 | 4.4 |
| $nC_{5+}$ | 20.2 | 17.4 | 17.4 |
| Rate (BPH) | 5305 | 6585 | 6585 |
| Debutanizer |  |  |  |
| Butane Product: |  |  |  |
| Rate (BPH) | 559 | 582 | 345 |
| Composition (Vol %) $iC_5$ | 6.25 | 2.94 | 3.00 |
| Heating duty (MMBTU/hr) | 44.5 | 68.0 | 94 |
| Cond duty (MMBTU/hr) | 41.6 | 51.2 |  |
| Sidedraw Rate (BPH Liq Eq) | 0 | 360 | 600 |
| Sidedraw recycled (BPH) |  | 300 | 300 |

EXAMPLE 2

An existing 60 MBSD debutanizer can recover and recycle up to 13 MBSD of isopentane at 66 percent purity (20 MBSD total sidedraw flow), while maintaining n-butane overhead purity at 95 percent. Reboiler duty is held constant to maintain the tower at a constant percent of flood, and additional feed preheat was added to handle the additional duty.

Very importantly, with 25 percent isopentane conversion across the reactor, the debutanized alkylate RVP is reduced from 4.33 PSI to only 2.88 PSI. The isopentane conversion reduces gasoline pool RVP by more than 70 M PSI barrels/ day and the low RVP alkylate improves gasoline blending flexibility. Debutanizer, reboiler and feed preheat duty increases by about 50 percent, but the isopentane vapor is condensed against alky depropanizer or deisobutanizer feeds.

Conditions before and after recycle are summarized as follows:

|  | BEFORE RECYCLE | AFTER RECYCLE |
|---|---|---|
| Debutanizer |  |  |
| DC4 feed: | 53,000 B/D | 61,160 B/D |
| Butane Comp (Vol %): |  |  |
| iC$_4$ | 4.0 | 4.0 |
| nC$_4$ | 95.0 | 95.0 |
| iC$_5$ | 1.0 | 1.0 |
| Duties (MMBTU/hr): |  |  |
| Condenser | 51.5 | 51.5 |
| Reboiler | 75.0 | 75.0 |
| Tower Preheat | 22.4 | 36.7 |
| iC5 Recycle Stream: |  |  |
| Rate (B/D) | 0 | 10,000 |
| Cond. Duty (MMBTU/hr) | 0 | 18.4 |
| Composition (Vol %): |  |  |
| nC$_4$ |  | 7.6 |
| iC$_4$ |  | 73.6 |
| nC$_{5+}$ |  | 18.8 |
| Recovery of iC$_5$ in draw (%): | 0 | 65.1 |
| RVP of alkylate (PSIA): | 4.33 | 3.50 |

EXAMPLE 3

Isopentane can be converted to low-RVP paraffins in an alkylation unit, but because of the low per-pass conversion rate, typically in the range of approximately 15 to 30 percent, most of any isopentane fed to an alkylation unit passes through unconverted and typically ends up in the debutanized alkylate. This limits the value of alkylating isopentane to reduce pool RVP, especially in a low-RVP RFG environment. This is because the debutanized alkylate is especially attractive as a low-RVP RFG blendstock. A volume of high-RVP isopentane can be converted to low-RVP alkylate, but only at the cost of shifting a substantially larger volume of unconverted high-RVP isopentane into the alkylate stream.

The shunting of isopentane to low-RVP alkylate can be reduced by removing isopentane from the high-RVP alkylate and recycling it to the alkylation unit. The usefulness of isopentane recycle can be seen by comparing four simulated cases at a 15 percent incremental conversion of feed isopentane.

| Case | 1 | 2 | 3 | 4 |
|---|---|---|---|---|
| Extraneous iC$_5$ Feed (MBSD) | 0 | 4.3 | 4.3 | 0 |
| iC$_5$ Recycled (MBSD) | 0 | 0 | 7.4 | 11.5 |
| Total iC$_5$ Feed (MBSD) | 0 | 4.3 | 11.7 | 11.5 |
| iC$_5$ in Reactor Effluent (MBSD) | 5.4 | 9.1 | 15.4 | 15.3 |

-continued

| Case | 1 | 2 | 3 | 4 |
|---|---|---|---|---|
| Net iC$_5$ Produced (MBSD) | 5.4 | 4.8 | 3.7 | 3.8 |
| ΔiC$_5$ in Pool (MSBD) | 0 | −0.6 | −1.7 | −1.6 |
| iC$_5$ in Total Alkylate (MSBD) | 5.4 | 4.8 | 3.7 | 3.8 |
| iC$_5$ in As-Produced Alkylate (MBSD) | 5.4 | 9.1 | ~0 | ~0 |
| RVP of As-Produced Alkylate (PSI) | 4.4 | 6.0 | <3 | <3 |
| Alkylate Rundown (MBSD) | 38.9 | 39.6 | 40.6 | 38.9 |

Case 1: No extraneous iC$_5$ alkylated/no iC$_5$ recycle
Case 2: 5 MBSD extraneous iC$_5$ alkylated/no iC$_5$ recycle
Case 3: 5 MBSD extraneous iC$_5$ alkylated/iC$_5$ recycle
Case 4: No extraneous iC$_5$ alkylated/iC$_5$ recycle Case 1 shows a significant amount of isopentane is produced in an alkylation unit. These 5.4 MBSD of isopentane contribute about 90 M RVP barrels per day to the gasoline pool and raise the RVP of the as-produced alkylate by about 2 PSI to 4.4 PSI.

Case 2 shows how the total isopentane in the gasoline pool can be reduced by alkylating 5 MBSD of an extraneous stream rich in isopentane on a once-through basis. The 0.6 MBSD reduction in pool isopentane, however, is offset by the low per-pass conversion of isopentane. An additional 3.7 MBSD of unconverted isopentane end up in the as-produced alkylate, thereby raising its RVP another 1.6 PSI to 6.0 PSI.

The low per-pass conversion of isopentane limits the usefulness of alkylating extraneous isopentane as an RVP control option. Low-RVP alkylate is an important blendstock for low-RVP reformulated gasoline. The RVP specification for Southern Gasoline is currently 7.1 PSI, and RVPs will likely go down in the future. It is not realistic for the RVP of the as-produced alkylate to be as great as or greater than the tightest gasoline RVP specification. If consuming 0.6 MBSD of isopentane in alkylation raises the RVP of alkylate 1.6 PSI to 6 PSI, then an upper limit of 7 PSI on the RVP of alkylate limits how much isopentane can be alkylated away on a one-through basis to about 1 MBSD at the outside.

The problem of unconverted isopentane can be ameliorated by recycling it. Because of the significant difference in volatility between the isopentane and the C7+ alkylate, a substantial fraction of the isopentane remaining in the alkylate can be recovered as a sidestream off the alky debutanizer and recycle to alkylation.

Case 3 shows the result of doing this. Recycle allows pool isopentane to be reduced by 1.7 MBSD, significantly more than would be practicable on a one-through basis. An additional benefit of separating out the isopentane in the alkylate is that the isopentane in the as-produced alkylate can be reduced indefinitely, or at least as low as separation costs make desirable, resulting in as-produced alkylate that has very low RVP. The blending flexibility offered by such a blendstock in a low RVP environment is valuable in itself.

Isopentane recycle makes the extraneous isopentane feed superfluous, as Case 4 shows. The amount of isopentane converted in Case 3 (1.7 MBSD) is small compared to the amount (5.4 MBSD) produced by the alkylation unit itself in Case 1. It is enough to recycle some or all of the isopentane produced in alkylation itself. Case 4 achieves all the benefits of Case 3 with a simpler scheme that dispenses with the extraneous isopentane source. Thus, with isopentane recovery and recycle, alkylation itself becomes the preferred source of the isopentane feed, eliminating the investment required to recover and route the extraneous isopentane to the alkylation unit.

EXAMPLE 4

Sulfuric acid-catalyzed isopentane/isobutane co-alkylation of butene/propylene using impure isopentane is compared to conventional isobutane alkylation, as summarized in Table 2, wherein the column labeled "Test" refers to isopentane/isobutane co-alkylation and the column labeled "Control" refers to conventional isobutane alkylation. In both cases identical reactor conditions and olefin feed composition are employed, but in the test case a low-purity feed of isopentane of the composition of Table 1 is added to the reactor feed. Table 2 shows the process conditions that are nearly identical, except that the isopentane:olefin ratio and $C_6+$:olefin ratios are higher for the test case. Tables 3 through 6 show key test results.

Comparing the test and control cases, the following advantages to the isopentane/isobutane co-alkylation process over conventional isobutane alkylation are:

high incremental isopentane conversion (49 percent)

insignificant changes in alkylate ASTM D-86 90% and end point decreased $C_{11}+$ yield small losses in isobutane consumption, $C_5+$ yield and octane low $C_6+$ alkylate density no significant increase in acid consumption Ordinarily, FCC $C_5$ and $C_6+$ materials greatly increase sulfuric acid consumption by as much as 1.0 lb/gal. Clearly isopentane and the $C_6+$ paraffins of isomerate have no impact on acid consumption.

These results, expressed per barrel of isopentane converted, are compared to Jurnegan's work in Table 8. They show clear yield and octane advantages for isobutane/isopentane co-alkylation over isopentane alkylation. In particular, for each barrel of isopentane converted in Jurnegan's work nearly one barrel of low-valued isobutane was produced and only 0.23 barrel of $C_6+$ was produced. In co-alkylation, each barrel of isopentane converted effectively produces 0.68 barrel of $C_6+$ and only 0.30 barrel of isobutane.

EXAMPLE 5

The isopentane byproduct of an Aromatics Recovery Unit is added to the isobutane-butene feed to a Stratco sulfuric acid alkylation unit. A summary of the results is shown in Table 9.

In this example, the incremental yield loss and octane loss is also small. Isopentane conversion was lower because of increased isobutane competition and lower reaction temperature. The yield and octane loss are about one-half the losses incurred by the Stratco method of reducing isopentane yield from amylenes, because of synergy between butenes and isopentane and operation at high total isoparaffin:olefin ratio.

In the Stratco method, FCC amylenes and isopentane are charged to an alky without butenes, and isopentane production is suppressed by reducing the isobutane recycle to the reactors. This results in a large octane loss of about 7 RON units per unit of isopentane converted, where RON is road octane number and an isobutane consumption loss of about 0.8 v/v of isopentane converted.

Figure 3:
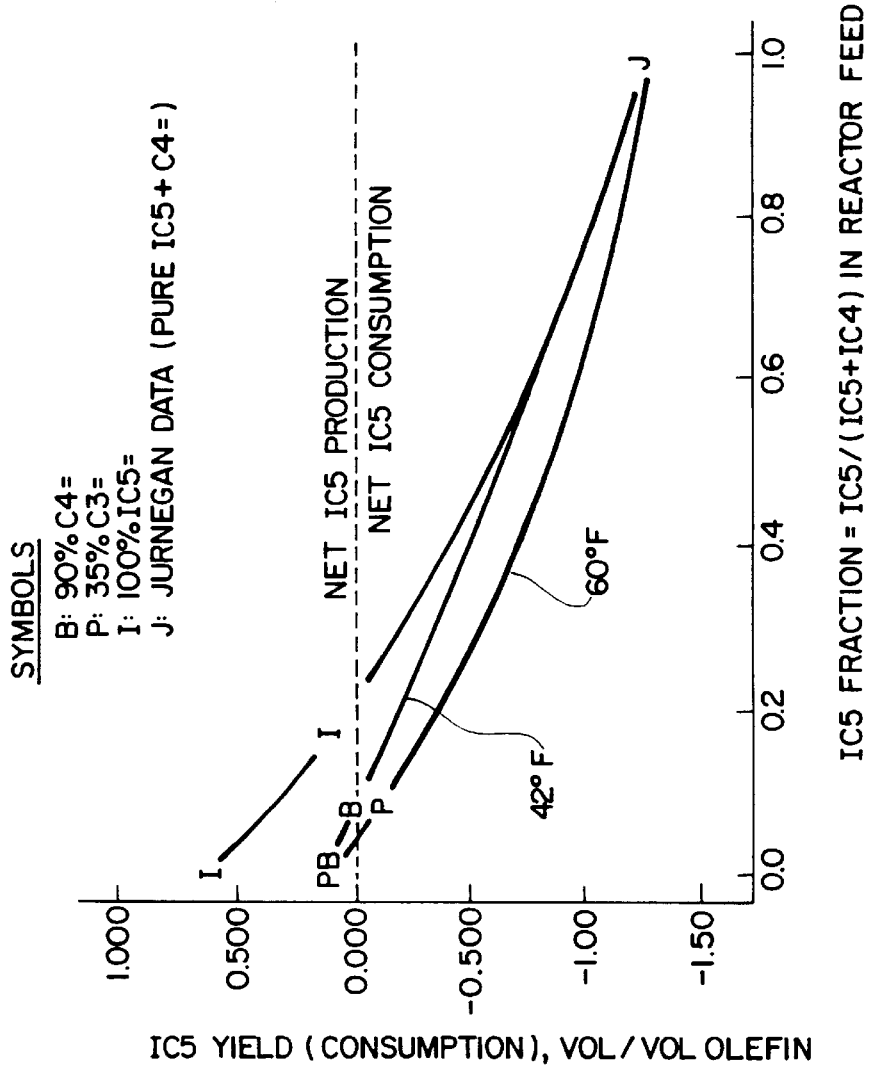
FIGS. 3 through 5 show the yield effects of added isopentane to sulfuric acid alkylation of C3 to C5 olefins.
Figure 4:
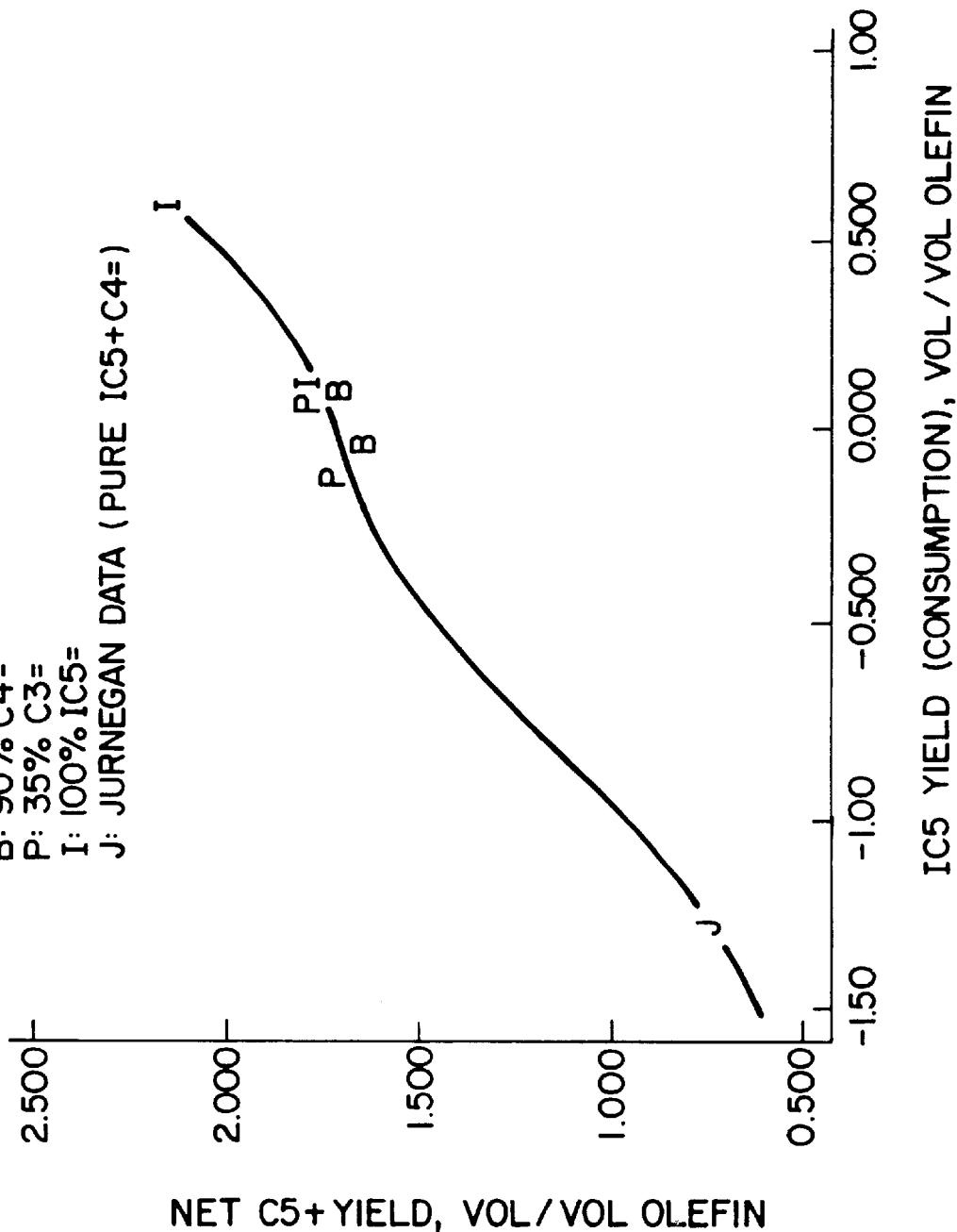
Figure 5:
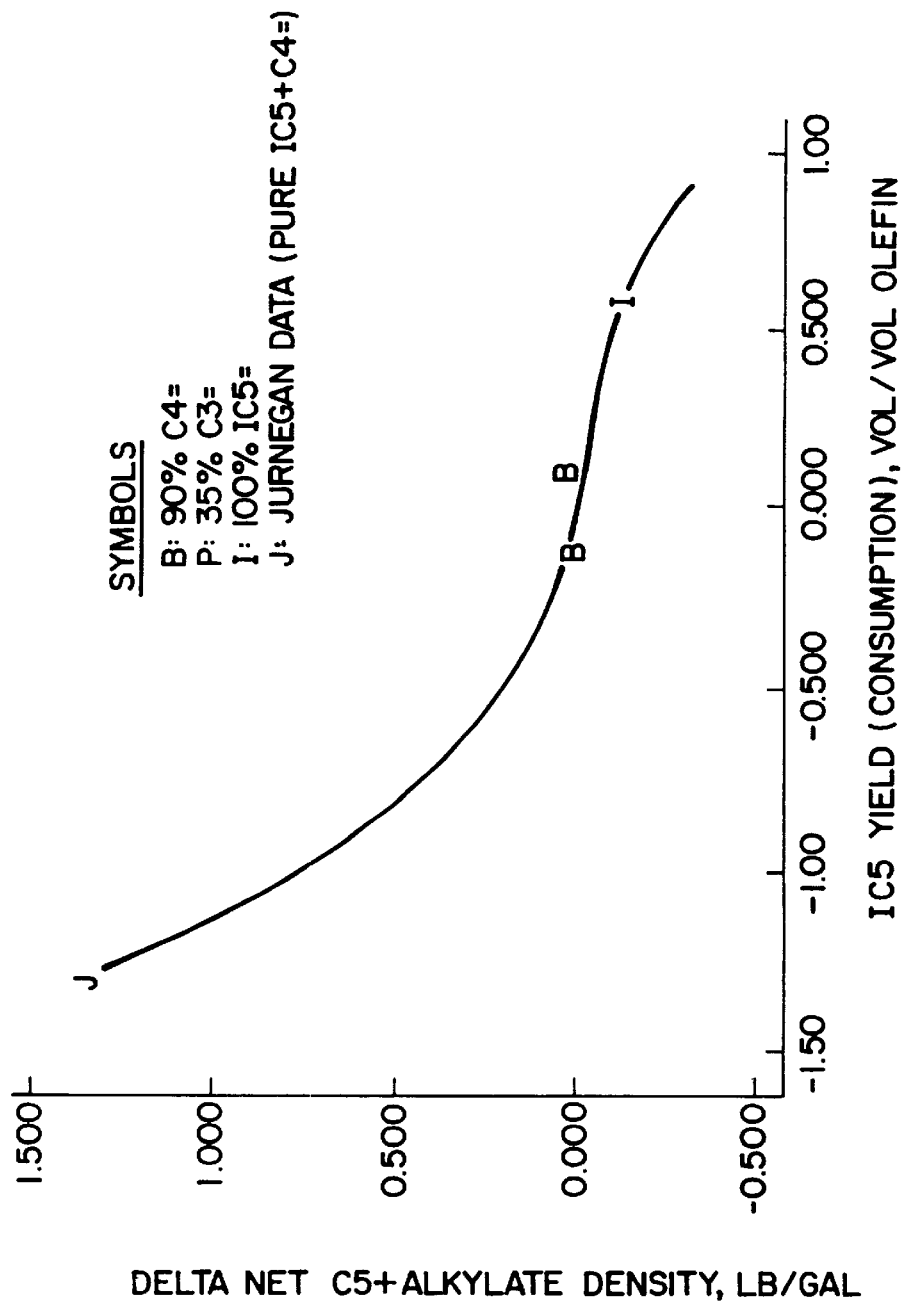

FIGS. 3 through 5 show the yield effects of added isopentane to sulfuric acid alkylation of $C_3$ to $C_5$ olefins. FIG. 3 is a graphical representation of isopentane yield (consumption) on olefin as a function of the fraction iC5/(iC5+iC4). Conversions of isopentane are highest at elevated reactor temperature and when the fraction of isopentane on total feed isoparaffins is high. Conversions in the range of approximately 15 to 49 percent have been observed for added isopentane.

FIG. 4 shows net $C_5+$ yield on olefin as a function of $iC_5$ yield (consumption). FIG. 5 shows net $C_5$ alkylate density as a function of $iC_5$ yield (consumption). It has been determined that the volumetric production of isopentane is under 0.2 v/v olefin, corresponding to an isopentane:olefin ratio of under 2 for most feeds and conditions.

Figure 6:
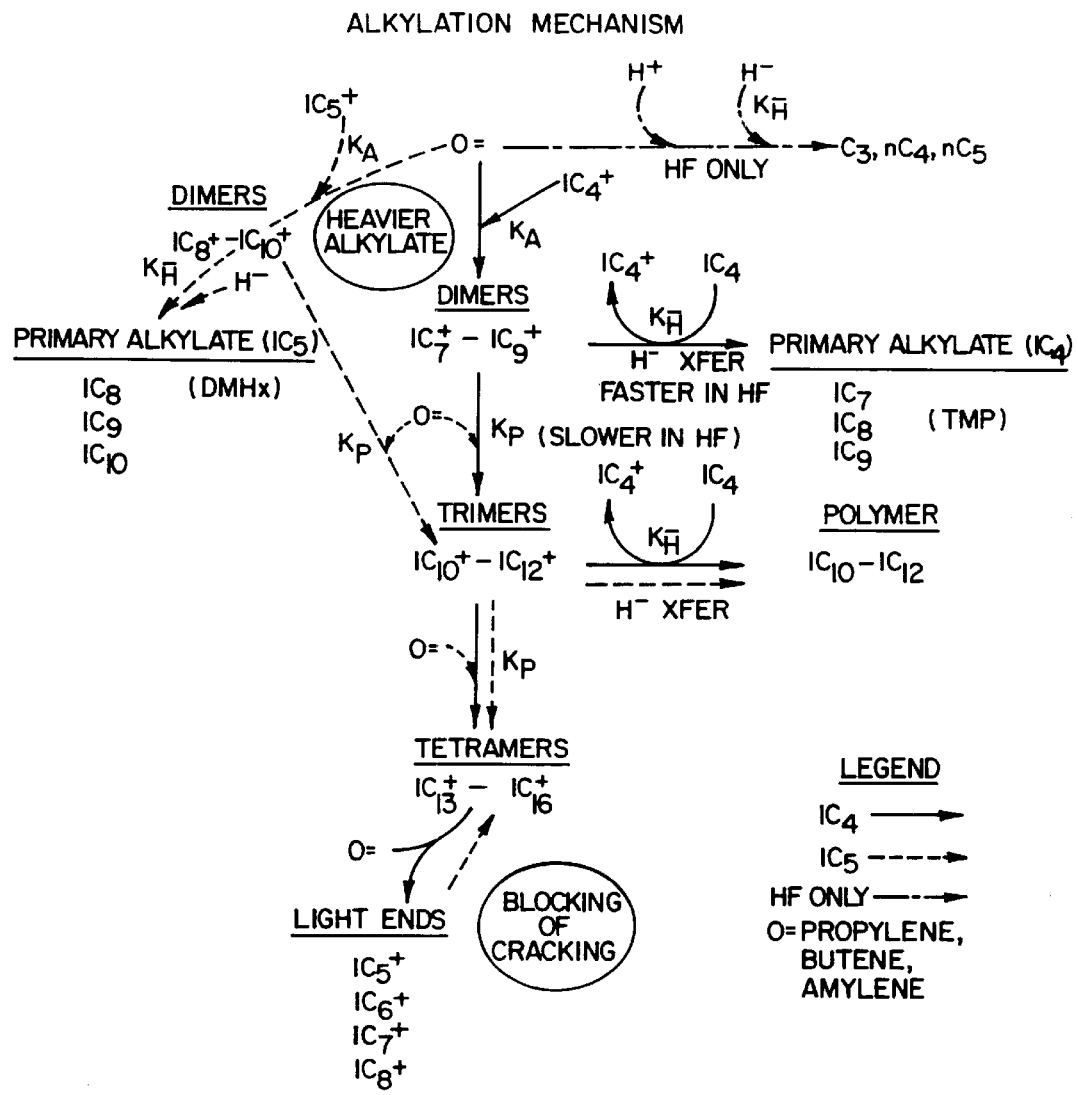
FIG. 6 shows a mechanism wherein the isopentane primarily blocks the cracking reactions of heavy ions to isopentane when the isopentane:olefin ratio is less than 2.

It is believed that in this regime, wherein the isopentane:olefin ratio is less than 2, added isopentane primarily blocks the cracking reactions of heavy intermediates to isopentane, as shown in the mechanism indicated in FIG. 6. Instead heavy intermediates appear to crack to iC6–iC8 paraffins. Direct competition with isobutane appears minor, since $C_5+$ yield and iC4 consumption are not greatly reduced. It is believed that in this case yields of isopentane decline. However, at high isopentane:olefin ratios, direct competition between isopentane and isobutane becomes more significant, resulting in net isobutane production and the low $C_5+$ yields of Jurnegan's work.

Thus there has been described herein methods and apparatus that are used in an alkylation reactor system for adding low purity isopentane to alky reactor feed to block formation of isopentane, resulting in high incremental isopentane conversion and minimal octane and $C_5+$ yield loss, and low acid consumption from $C_6+$ isoparaffins with superior yields.

TABLE 1

Light Isomerate Composition and Alkylation Feed Level

| Light Isomerate | Volume Percent | | Wt./Wt. Olefin in Feed |
| --- | --- | --- | --- |
| | Commercial | Test | Test |
| iC4 | 0.7 | N/A | N/A |
| nC4 | 1.0 | N/A | N/A |
| iC5 | 73.0 | 72.6 | 0.528 |
| nC5 | 2.3 | 5.7 | 0.042 |
| 2.2 DMB | 5.4 | 4.5 | 0.033 |
| cC5 | 2.0 | 1.3 | 0.010 |
| 2.3 DMB | 2.1 | 1.6 | 0.013 |
| 2 MP | 7.7 | 6.4 | 0.047 |
| 3 MP | 4.4 | 3.7 | 0.027 |
| MCP | 1.0 | 1.8 | 0.013 |
| Other C6 | 0.1 | 0.3 | 0.002 |
| C7+ | 0.3 | 0.1 | 0.000 |

TABLE 2

Feed Properties and Process Conditions

| Feed Properties: | Control | Test |
|---|---|---|
| Propylene (wt/wt olefin) | 0.213 | 0.230 |
| Isobutlylene (wt/wt olefin) | 0.037 | 0.036 |
| N-butylene (wt/wt olefin) | 0.750 | 0.734 |
| Amylenes (wt/wt olefin) | 0.000 | 0.000 |
| Isopentane (wt/wt olefin) | 0.029 | 0.528 |
| C6+ paraffins (wt/wt olefin) | 0.000 | 0.145 |
| Reactor conditions: | | |
| Reactor temperature (F.) | 59.4 | 59.5 |
| Acid strength (wt %) | 89.16 | 89.11 |
| Reactor acid fraction (vol) | 0.454 | 0.45 est. |
| LHSV | 0.305 | 0.30 est. |
| Isobutane conc. in effluent (vol %) | 0.629 | 0.639 |
| Injector nozzle conditions: | | |
| Injector nozzle temperature (F.) | 35.8 | 36.7 |
| Injector nozzle olefin conc. (wt %) | 12.3 | 11.9 |

TABLE 3

Key Results

| | Control | Test | Change | Std. Dev. |
|---|---|---|---|---|
| Net C5+ yield (wt/wt) | 2.098 | 2.028 | −0.070 | 0.044 |
| Isopentane yield (wt/wt) | 0.104 | −0.104 | −0.258 | 0.162 |
| Isobutane consumption (wt/wt) | 1.096 | 1.024 | −0.072 | 0.039 |
| Net C5+ RON | 94.29 | 93.99 | −0.30 | 0.31 |
| Net C5+ MON | 91.72 | 91.03 | −0.69 | 0.52 |
| Net C5+ RVP (psi) | 4.23 | 1.51 | −2.71 | 2.33 |
| Net C5+ density (lb/gal) | 5.858 | 5.897 | 0.039 | 0.039 |
| Net C5+ molecular weight | 109.0 | 119.6 | 10.6 | 6.5 |
| Net C5+ endpoint (F.) | 368.7 | 370.8 | 2.1 | 8.3 |
| ADF titration (lb/gal net C5+) | 0.079 | 0.094 | 0.015 | 0.026 |
| ADF analytical (lb/gal net C5+) | 0.052 | 0.059 | 0.007 | 0.016 |
| Mass balance on olefin (wt %) | 91.0 | 85.6 | — | — |
| n-butane balance on feed (wt %) | 98.9 | 97.4 | — | — |

TABLE 4

Net C5+ Alkylate Properties and Yields

| | Control | Test | Change | Std. Dev. |
|---|---|---|---|---|
| Yields/Consumption: | | | | |
| Net C5+ yield (wt/wt olefin) | 2.098 | 2.028 | −0.070 | 0.044 |
| Net C5+ yield (vol/vol olefin) | 1.757 | 1.688 | −0.069 | N/A |
| iC5 yield (wt/wt olefin) | 0.104 | −0.154 | −0.258 | 0.162 |
| iC5 yield (wt/wt olefin) | 0.0981 | −0.145 | −0.243 | N/A |
| iC4 consump. (wt/wt olefin) | 1.096 | 1.024 | −0.072 | 0.039 |
| iC4 consump. (vol/vol olefin) | 1.147 | 1.072 | −0.075 | N/A |
| Net C5+ Alkylate Properties: | | | | |
| RON | 94.29 | 93.99 | −0.30 | 0.31 |
| MON | 91.72 | 91.03 | −0.69 | 0.52 |
| RVP (psi) | 4.23 | 1.51 | −2.71 | 2.33 |
| Density (lb/gal) | 5.858 | 5.897 | 0.039 | 0.039 |
| Molecular weight | 109.0 | 119.6 | 10.6 | 6.5 |
| Molar volume | 0.443 | 0.481 | 0.038 | 0.026 |
| T10 (F) | ~170 | ~175 | ~5 | N/A |
| T50 (F) | ~225 | ~220 | ~5 | N/A |
| T90 (F) | ~275 | ~280 | ~5 | N/A |
| Endpoint (F) | 368.7 | 370.8 | 2.1 | 8.3 |

TABLE 5

Net C5+ Alkylate Properties and Yields

| | Control | Test | Change | Std. Dev. |
|---|---|---|---|---|
| Yields: | | | | |
| Net C6+ yield (wt/wt olefin) | 1.993 | 2.182 | 0.188 | 0.155 |
| Net C6+ yield (vol/vol olefin) | 1.659 | 1.828 | 0.169 | N/A |
| Net C6+ Alkylate Properties: | | | | |
| RON | 94.41 | 93.85 | −0.56 | 0.44 |
| MON | 91.80 | 90.96 | −0.84 | 0.51 |
| RVP (psi) | 3.18 | 3.09 | −0.09 | 0.76 |
| Density (lb/gal) | 5.898 | 5.857 | −0.04 | 0.08 |
| Molecular weight | 112.0 | 114.0 | 2.0 | 1.0 |
| Molar volume (bbl/lbmol) | 0.453 | 0.464 | 0.011 | 0.011 |
| Endpoint | 368.7 | 370.8 | 2.1 | 8.3 |

TABLE 6

Net Speciated Alkylate Yields

| Net Yields (wt/wt olefin) | Control | Test | Change | Std. Dev. |
|---|---|---|---|---|
| isopentane | 0.104 | −0.154 | −0.258 | 0.162 |
| C6 isoparaffins | 0.114 | 0.040 | −0.073 | 0.074 |
| C7 isoparaffins | 0.388 | 0.440 | 0.052 | 0.023 |
| trimethylpentanes | 1.068 | 1.166 | 0.097 | 0.181 |
| low octane C8 isoparaffins | 0.189 | 0.216 | 0.027 | 0.021 |
| trimethylhexanes | 0.049 | 0.110 | 0.061 | 0.013 |
| low octane C9 isoparaffins | 0.037 | 0.060 | 0.023 | 0.007 |
| C10 isoparaffins | 0.056 | 0.068 | 0.012 | ~0.030 |
| C11 isoparaffins | 0.061 | 0.065 | 0.004 | ~0.036 |
| C12+ isoparaffins | 0.030 | 0.016 | −0.014 | ~0.022 |

TABLE 7A

Alkylate Properties and Yields: Test Minus Control Test Data Compared with Predictions from Jernigan Data

| | Test | Jernigan | Difference |
|---|---|---|---|
| Delta Yields/Consumption: | | | |
| Net C5+ yield (vol/vol olefin) | −0.070 | −0.075 | 0.005 |
| iC5 yield (vol/vol olefin) | −0.258 | ~−0.17 | ~−0.088 |
| iC4 consump. (vol/vol olefin) | −0.072 | ~−0.82 | −0.010 |
| Delta Net Alkylate Properties: | | | |
| RON | −0.30 | −0.72 | 0.42 |
| MON | −0.70 | −0.60 | −0.10 |
| RVP (psi) | −2.71 | ~−1.18 | ~−1.53 |

TABLE 7B

Alkylate Composition: Test Data Compared with Predictions from Jernigan Data

| Volume Percent | Test | Jernigan | Difference |
|---|---|---|---|
| C6 isoparaffins | 2.26 | 5.45 | −3.19 |
| C7 isoparaffins | 20.22 | 18.80 | 1.42 |

TABLE 7B-continued

Alkylate Composition: Test Data Compared with Predictions from Jernigan Data

| Volume Percent | Test | Jernigan | Difference |
|---|---|---|---|
| trimethylpentanes | 52.94 | 54.86 | −1.92 |
| low octane C8 isoparaffins | 9.86 | 8.40 | 1.46 |
| trimethylhexanes | 5.05 | 4.37 | 0.68 |
| low octane C9 isoparaffins | 2.78 | 1.18 | 1.59 |
| C10+ isoparaffins | 6.89 | 6.93 | −0.04 |

TABLE 8

| Feed | iC4/iC5 Alky C3=/C4= | iC5 Alky (Jurnegan) C4= |
|---|---|---|
| Temperature (F.) | 60.0 | 42.0 |
| Olefin LHSV | 0.3 | 0.2 |
| iC4:Olefin | 6.0 | 0.0 |
| iC5:Olefin | 0.5 | 4.6 |
| Isopentane Convrsn. (%) | 49 | 25 |
| Incremental Yields and Properties per Volume of iC5 Converted | | |
| iC5 | −1.00 | −1.00 |
| iC4 | 0.29 | 1.00 |
| C6+ | 0.68 | 0.23 |
| Net C5+ | −0.3 | −0.7 |
| C6+ Density | 0.68 | 0.72 |
| RM/2 | −2.3 | −4.4 |

TABLE 9

Incremental Yields of Commercial Isopentane Alkylation

| iC4: Olefin Ratio | 10 |
|---|---|
| Delta iC5: Olefin Ratio | 0.8 |
| Temperature (F.) | 42 |
| iC5 Convrsn. Ylds. on iC5 Convrtd. (%) | 16–19 |
| Delta iC4/Delta iC5 | 0.39 |
| Delta C5+/Delta iC5 | −0.37 |
| Delta C6+/Delta iC5 | 0.63 |
| Delta RM2/Delta iC5 | −1.7 |

What is claimed is:

1. A method of alkylating a mixture of $C_3$ to $C_5$ olefins with an acid catalyst to form a high octane alkylate that has relatively low Reid vapor pressure, comprising the steps of:
   (a) charging a mixed $C_3$ to $C_5$ olefins stream with an isobutane stream to form an isobutane-charged alkylation feed having an isobutane to olefin ratio by volume of above 5;
   (b) charging said isobutane-charged alkylation feed with an isopentane stream to form a mixed paraffin-charged alkylation feed having an isopentane to olefin ratio by volume in the range of 0.1 to 2.0;
   (c) reacting said mixed paraffin-charged alkylation feed through contact with an acid catalyst to form an alkylate;
   (d) removing propane from said alkylate in a depropanizing operation to form a depropanized alkylate;
   (e) removing isobutane from said depropanized alkylate to yield recovered isobutane and a deisobutanized and depropanized alkylate;
   (f) removing butane and isopentane from said deisobutanized and depropanized alkylate to yield an alkylate product which exhibits a Reid vapor pressure of is less than 3.0 psi and has high octane;
   (g) deriving at least a portion of said isobutane stream used in step (a) from said recovered isobutane from step (e); and
   (h) deriving at least a portion of said isopentane stream used in step (b) from the isopentane which is removed in step (f), and substantially all of the of isopentane removed in step (f) is used in the isopentane stream of step (b).

2. The method set forth in claim 1, wherein the propane removal step (d) comprises a flashing operation.

3. The method set forth in claim 1, wherein step (f) comprises a multistage distillation operation in which the isopentane is removed in a side stream.

4. An alkylation process which comprises:
   (a) delivering isobutane, isopentane and an olefin feed to a reaction zone at an isobutane to olefin ratio by volume of above 5 and an isopentane to olefin ratio by volume in the range of 0.1 to 2.0, wherein said, olefin feed is comprised of at least one olefin selected from the group consisting of $C_3$ to $C_5$ olefins;
   b) contacting the isobutane and isopentane with the olefin feed in the presence of an alkylation catalyst under conditions which are effective to produce a $C_6+$ alkylate by the reaction of the isobutane and isopentane with the olefin feed, wherein said contacting is carried out within the reaction zone;
   (c) withdrawing an effluent from the reaction zone which comprises $C_6+$ alkylate and isopentane, wherein at least a portion of said isopentane is produced by said reaction in the reaction zone;
   (d) separating a major portion of the isopentane from said effluent and additionally removing propane, butane and isobutane from said effluent to produce an alkylation product which exhibits a Reid vapor pressure of is less than 3.0 psi; and
   (e) recycling substantially all of said separated isopentane to the reaction zone so that a major portion of the isopentane delivered to the reaction zone is comprised of said separated isopentane.

5. The process of claim 4 wherein the olefin feed is comprised of a mixture of $C_3$ to $C_5$ olefins.

6. The process of claim 4 wherein substantially all of the isopentane delivered to the reaction zone is comprised of isopentane which has been separate from said effluent.

7. The process of claim 4 wherein substantially all of the isopentane is separated from said effluent.

8. The process of claim 7 wherein said isopentane is separated from the effluent as a side stream from a debutanizer.

9. A method of alkylating a mixture of $C_3$ to $C_5$ olefins with an acid catalyst to form a high octane alkylate that has relatively low Reid vapor pressure, comprising the steps of:
   (a) charging a mixed $C_3$ to $C_5$ olefins stream with an isobutane stream to form an isobutane-charged alkylation feed having an isobutane to olefin ratio by volume of above 5;
   (b) charging said isobutane-charged alkylation feed with an isopentane stream to form a mixed paraffin-charged alkylation feed having an isopentane to olefin ratio by volume in the range of 0.1 to 2.0;
   (c) reacting said mixed paraffin-charged alkylation feed through contact with an acid catalyst to form an alkylate;

(d) removing propane from said alkylate in a depropanizing operation to form a depropanized alkylate;

(e) removing isobutane from said depropanized alkylate to yield recovered isobutane and a deisobutanized and depropanized alkylate;

(f) removing butane and isopentane from said deisobutanized and depropanized alkylate by means comprising a multistage distillation operation in which the isopentane is removed in a side stream to yield an alkylate product which exhibits a Reid vapor pressure of is less than 3.0 psi and has high octane;

(g) deriving at least a port on of said isobutane stream used in step (a) from said recovered isobutane from step (e); and substantially all of the sidestream of isopentane in step (f) is used in the isopentane stream of step (b).

10. The method set forth in claim 9, wherein the propane removal step (d) comprises a flashing operation.

* * * * *

UNITED STATES PATENT AND TRADEMARK OFFICE
CERTIFICATE OF CORRECTION

PATENT NO.      : 6,429,349 B1
DATED           : August 6, 2002
INVENTOR(S)     : Lewis E. Grimes et al.

It is certified that error appears in the above-identified patent and that said Letters Patent is hereby corrected as shown below:

Column 3,
Line 12, "acids generally that are commonly used" should read -- acids are commonly used --
Lines 45 and 46, "in an output steam 80." should read -- in an output stream 80. --

Column 4,
Line 4, "atoms per molecule Terms" should read -- atoms per molecule. Terms --
Line 13, "barrels (of 42 gallon each)" should read -- barrels (of 42 gallons each) --
Line 36, "$nC_4$" should read -- $nC_3$ --
Line 38, "$nC_5$" should read -- $nC_4$ --

Column 5,
Line 31, "$iC_4$" should read -- $iC_5$ --

Column 6,
Line 17, "shows a significant amount" should read -- shows that a significant amount --
Line 47, "and the C7+ alkylate," should read -- and the $C_7$+ alkylate, --
Line 50, "and recycle to alkylation." should read -- and recycled to alkylation. --

Column 7,
Line 17, "both cases identical reactor" should read -- both cases, identical reactor --

Column 8,
Line 22, "net $C_5$ alkylate density" should read -- net $C_5$+ alkylate density --
Line 42, "Thus there has been described" should read -- Thus, there has been described --

Column 9,
Line 54, "~225    ~220    ~5    N/A" should read -- ~225    ~220    ~-5    N/A --

UNITED STATES PATENT AND TRADEMARK OFFICE
CERTIFICATE OF CORRECTION

PATENT NO. : 6,429,349 B1
DATED : August 6, 2002
INVENTOR(S) : Lewis E. Grimes et al.

It is certified that error appears in the above-identified patent and that said Letters Patent is hereby corrected as shown below:

Column 10,
Line 20, "5.898   5.857   -0.04   0.08" should read
-- 5.896   5.857   -0.04   0.08 --
Line 52, "-0.072   ~-0.82   -0.010" should read -- -0.072   ~-0.82   ~0.010 --

Column 11,
Line 21, "49   25" should read -- 49   ~25 --
Line 63, "vapor pressure of is less" should read -- vapor pressure of less --

Column 12,
Line 16, "wherein said, olefin feed is" should read -- wherein said olefin feed is --
Line 35, "vapor pressure of is less" should read -- vapor pressure of less --
Line 46, "separate from said effluent." should read -- separated from said effluent. --

Column 14,
Line 1, "vapor pressure of is less" should read -- vapor pressure of less --
Line 3, "at least a port on of" should read -- at least a portion of --

Signed and Sealed this

First Day of July, 2003

JAMES E. ROGAN
*Director of the United States Patent and Trademark Office*